United States Patent [19]

Bolton

[11] Patent Number: 4,946,388

[45] Date of Patent: Aug. 7, 1990

[54] DENTAL ARTICULATOR MOUNTING FOR DENTAL CASTS

[76] Inventor: Wayne A. Bolton, 5302 Scenic Dr., Yakima, Wash. 98908

[21] Appl. No.: 146,414

[22] Filed: Jan. 21, 1988

[51] Int. Cl.⁵ ............................................. A61C 11/00
[52] U.S. Cl. ......................................... 433/56; 433/65
[58] Field of Search ....................... 433/54, 55, 56, 65, 433/60, 34

[56] References Cited

U.S. PATENT DOCUMENTS

| 90,706 | 6/1869 | Bonhorst | 433/55 |
| 1,498,559 | 6/1924 | Lightcap | 433/56 |
| 2,219,559 | 10/1940 | Lentz | 433/55 |
| 2,748,481 | 6/1956 | Glueck | 433/55 |
| 3,043,009 | 7/1962 | Whitman | 433/49 |
| 3,823,476 | 7/1974 | Hudson et al. | 433/54 |
| 4,624,639 | 11/1986 | Wong | 433/55 |

Primary Examiner—John Weiss
Assistant Examiner—Adriene J. Lepiane
Attorney, Agent, or Firm—Roy E. Mattern, Jr.

[57] ABSTRACT

A dental articulator, having an interim used tripod, reproduces the relationships of the jaws and teeth of respective dental patients. Their upper or maxillary jaw and their lower or mandibular jaw dental casts are positionable in their neuromuscular resting position, or in their full teeth contacting centric occlusion position. Lower and upper trays, are formed like art portions of full display dental casts, and adjustably connected together in opposed disposition, by a U shaped rigid upright support. Dental plaster is used to position and to secure the lower dental cast in the lower tray, while also using, during this interim, a tripod especially preadjusted to the cant of the occlusal plane of a patient's teeth, as determined and recorded from an observance of a patient's lateral cephalometric head X-ray film.

10 Claims, 3 Drawing Sheets

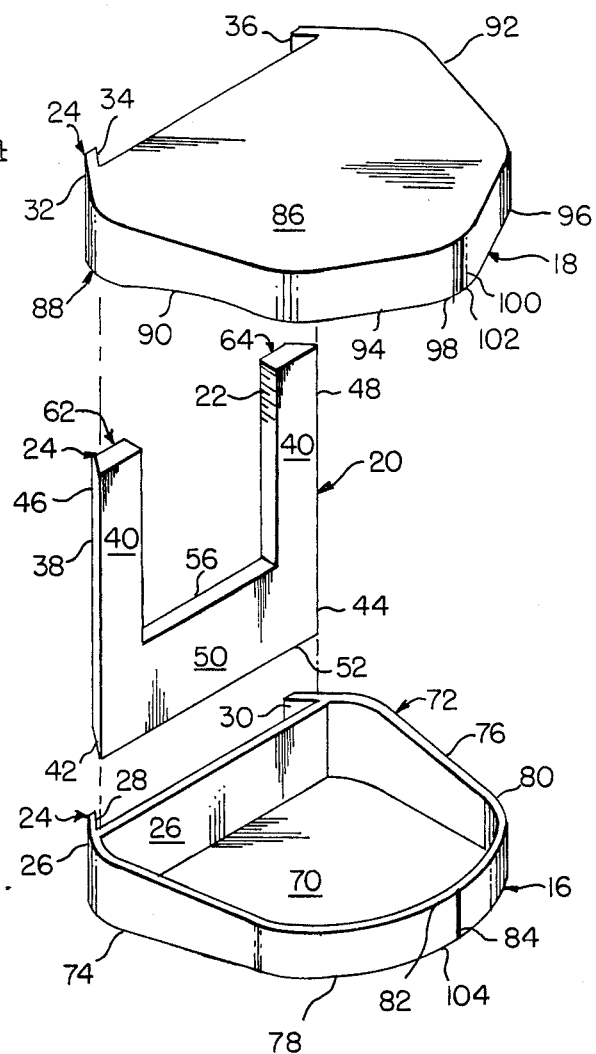
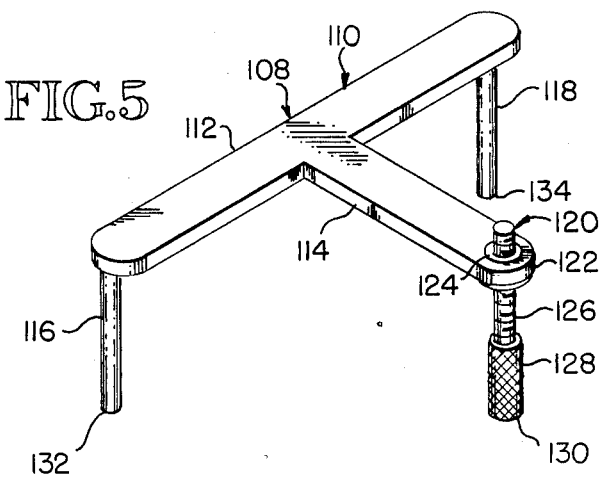

4,946,388

DENTAL ARTICULATOR MOUNTING FOR DENTAL CASTS

BACKGROUND OF INVENTION

It is understood Mr. Whitman in 1962 in his U.S. Pat. No. 3,043,009, provided plastic trays to create standard structural bases or art portions, to thereafter receive dental casts, and thereby eliminate the need for making full display dental casts with bases trimmed by using rotary grinders.

Then in 1974 Robert Hudson and John Richards in their U.S. Pat. No. 3,823,476 in addition to providing plastic trays, provided a pivotal connection between such trays creating a hinge motion to simulate the relative movement of a patient's upper and lower jaws.

SUMMARY OF THE INVENTION

A dental articulator mounting of dental casts, and a method of its use are provided to reproduce the relationships of the jaws and teeth of a respective dental patient. Although the full teeth contacting position, also referred to as the centric occlusion position, is readily reproducible using this dental articulator mounting of dental casts, it is particularly useful in readily reproducing the neuromuscular resting position of a patient's jaws and teeth.

By observing a patient's lateral cephalometric head X-ray film, the cant of the occlusal plane of a patient's teeth is observable or determinable. This cant information is thereafter used in securing a lower jaw and teeth dental cast of a patient in a lower tray of the general appearance of those previously used by other dentists to avoid the use of full display dental casts, which were trimmed by using rotary grinders.

This dental articulator mounting includes receptacles, designated as a lower tray and an upper tray, which are specifically different, but which have a somewhat general appearance. Each tray at the rear has spaced dovetailed receiving portions, which are vertically orientated. A U shaped upstanding rigid support has spaced vertically extending legs or columns dovetailed to frictionally and slidably enter the dovetailed spaced vertical receiving portions at the rear of each tray.

A tripod is used during an interim period of positioning a lower jaw and teeth dental cast in the lower tray using dental plaster. The tripod is angularly set to match a cant of the occlusal plane of a patient's jaws and is positioned over lower teeth to determine the correct cant, as this lower dental cast is being manipulated before the dental plaster hardens.

Then to determine the full teeth contact positioning of the dental casts, also referred to as the centric occlusion, the upper dental cast is related to the lower dental cast by using a bite registration taken with the patient's teeth clenched firmly together. The combination of this bite registration and the upper dental cast is placed on the respective lower teeth guided by the indentations of the bite registration, thus completing the establishment of the relation between upper and lower teeth and jaws. Then the soft dental plaster is placed on the top of the upper dental cast. Thereafter, the upper tray, guided by the legs or columns of the U shaped rigid upright support, is gently lowered into the soft plaster, until the level of the base of the upper tray and the top of the U shaped upright support columns are flush.

Or, thereafter alternatively, to create the neuromuscular resting position of the patient's jaws, the laboratory procedure is almost identical to the full teeth contacting position. However instead of using a bite registration, a tooth guided jaw registration is used. This jaw registration is obtained, preferably through the use of electronic muscle relaxing and jaw tracking instrumentation, with the patient's muscles at rest, during the formation of this jaw registration.

Subsequently, if a dentist desires to keep the history of a patient's jaw and teeth relationships in both the full teeth closed position and the neuromuscular resting position, then the dentist arranges sets of the trays into their respective upper and lower positions with their dental casts in place, one set showing the full teeth closed position and the other set showing the neuromuscular position. In the set showing the neuromuscular resting position, with the jaw registrations in place, or stated differently with the rest positions in place, the dentist observes the spacing indicia on the U shaped support, and records the measurements. Thereafter, the jaw or resting position registrations are removed, and the neuromuscular resting position is always reachable again by arriving at the same spacing, known as the freeway space, between the upper and lower teeth and their jaws, when in their resting position.

By using this dental articulator, the horizontal, vertical, and transverse relationships of a patient's jaws and teeth are reproducible and then observable in the absence of a patient, for current and subsequent study in providing dental care. Such observance is especially valuable in the practice of orthodontics.

DRAWINGS OF THE PREFERRED EMBODIMENT

The dental articulator mounting with its interim use tripod, and their method of use are illustrated in the drawings, wherein:

FIG. 4 is a perspective and exploded view of the three interfitting portions of the dental articulator mounting: the lower receptacle designated as the lower tray; the U shaped upright support with the spacing indicia, and the upper receptacle, designated as the upper tray;

FIG. 5 is a perspective view of the tripod, used in an interim period, when a lower dental case is being positioned in dental plaster in a lower tray at the cant position of the lower occlusal plane of a patient's teeth;

Figure 6:
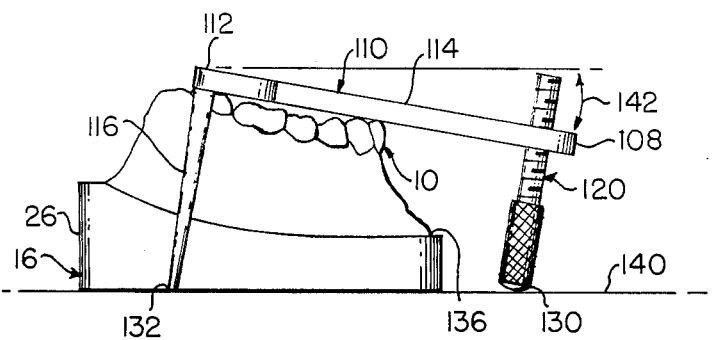
Figure 7:
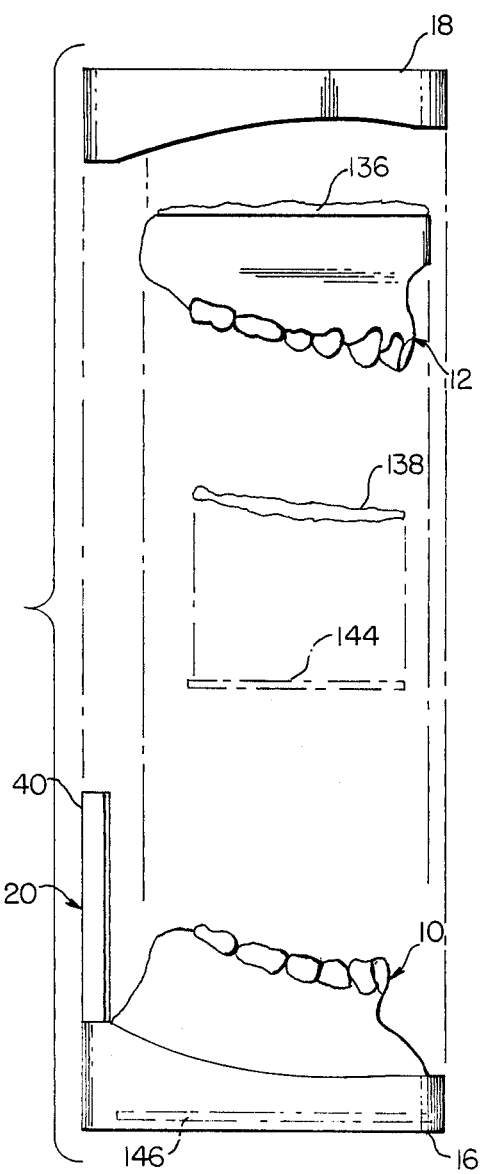

FIG. 6 is a side view of the tripod, shown in FIG. 5, as this tripod is being used to be adjusted to the cant of the lower occlusal plane, and thereafter to be used to set a patient's lower dental cast at this same cant of the lower occlusal plane in dental plaster in the lower tray of this dental articulator; and FIG. 7 is an exploded schematic view to illustrate how the positioning of the patient's upper dental cast is accomplished using, alternatively, either a full bite registration in later acquiring the centric occlusion, or a jaw or rest position registration in later acquiring the neuromuscular rest position, as soft dental plaster is placed on the top of the patient's upper dental cast, followed by lowering the upper tray guided by the legs or columns of the U shaped support to the flush position.

DESCRIPTION OF THE PREFERRED EMBODIMENTS AND THE METHOD OF USE OF DENTAL ARTICULATOR

Completed Mounting Using the Dental Articulator

Figure 1:
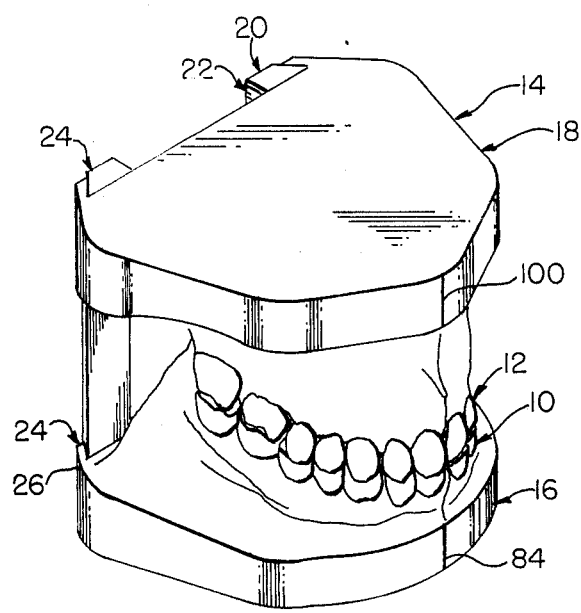
FIG. 1 is a perspective view of the dental articulator in which a patient's upper and lower dental casts have been secured as positioned in a full teeth contacting position, also referred to as the centric occlusion position.
Figure 2:
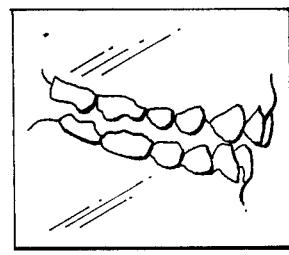
FIG. 2 is a schematic portion of a patient's lateral cephalometric head X-ray film, which is used initially to determine the cant of the lower occlusal plane of a patient's teeth in their neuromuscular rest position.
Figure 3:
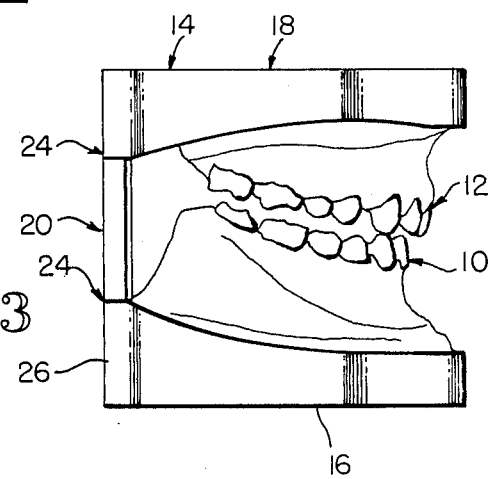
FIG. 3 is a side view of the dental articulator mounting holding a patient's upper, i.e. maxillary, and lower, i.e. mandibular, dental casts in place in a patient's neuromuscular rest position.

The completed mounting of a patient's upper and lower dental casts, 10 and 12, using the dental articulator 14 is illustrated in FIG. 1, as these casts are positioned in their full teeth contacting position, also referred to as the centric occlusion position. A schematic view is illustrated in FIG. 2, of a portion 15 of a patient's lateral cephalometric head X-ray film, which is observed by a dentist to initially determine the cant of the occlusal plane of a patient's teeth in their neuromuscular rest position. As shown in FIG. 3, the patient's upper and lower dental casts, 10 and 12, are positioned in their neuromuscular rest position while supported by the dental articulator 14.

Three Interfitting Portions of the Dental Articulator

The three interfitting removable portions of this dental articulator 14, are illustrated in FIG. 4, before their assembly. They are the receptacles, designated as the lower tray 16 and upper tray 18, and the U shaped upright support 20 having the spacing indicia 22, used in measuring the space between the patient's lower dental cast 10, and the upper dental cast 12, which is also referred to as the freeway space. This freeway space is the same freeway space which is present when the patient's jaws and teeth are in their neuromuscular rest position.

These three interfitting removable portions, each have portions of dovetail interfitting portions 24. The lower tray 16 has a higher back 26, which has spaced dovetail receivers 28, 30. The upper tray 18 has a higher back 32, not quite as high as the higher back 26 of the lower tray 16, which also has spaced dovetail receivers 34, 36. Then the U shaped upright support 20 has its outer vertical edges 38 and portions 40 formed as spaced dovetail inserting portions 42, 44, below, and 46, 48, above, to be frictionally and slidably inserted in the spaced dovetail receivers 28, 30, 34, 36 of the trays 16, 18.

This U shaped upright support 20 has a bottom cross member 50, sized so the outer dovetail vertical edges 38 and portions 40 thereof very firmly fit the dovetail receivers 28, 30 of the lower tray 16. This bottom cross member 50 is continuous along its bottom 52 and along its top 56. Then there are prespaced flexible upstanding columns or legs 62, 64 of the U shaped upright support 20, which comprise the combined upstanding portions 40 and the outer dovetail vertical edges 38.

This arrangement of dovetail portions 24 on their respective parts permits the precise vertical positioning of the upper tray 18 with respect to the lower tray 16. Like measurement indicia 22 also called spaced indicia 22 is provided on each upstanding leg 62, 64, as shown in FIG. 4, so the selected spaced positions of these trays 16 and 18 are observed and recorded.

Although these lower and upper trays 16, 18, which are slidably and frictionally positioned in an opposed relationship on the U shaped upright support 20, using the respective dovetail structures 24, appear to be basically similar in design, there are differences. They are shaped to conform in appearance to respective art portions of full display dental casts, which have been previously typically trimmed by using rotary grinders.

The lower tray 16 has a flat base 70 with a completely encircling upstanding wall structure 72 about the periphery thereof. The rear or back wall portion 26 of the wall structure 72 is higher than both the like height lateral wall portions 74, 76 and the like height medial wall portions 78, 80. These lateral wall portions 74, 76 upon leaving the back wall portion 26, decrease in height, as they converge forwardly to meet the medial wall portions 78, 80. From this junction of the lateral wall portions 74, 76, and the medial wall portions 78, 80, the medial wall portions 78, 80 increase slightly in height, in reaching an apex 82 at the front centerline 84 of the lower tray 16.

In a somewhat similar way, the upper tray 18, has a flat top 86 completely encircling depending wall structure 88 about the periphery thereof. The rear or back wall portion 32 of the wall structure 88 is deeper than both the like depth lateral wall portions 90, 92 and the like depth medial wall portions 94, 96. These lateral wall portions 90, 92, upon leaving the back wall portion, 32, decrease in depth as they converge forwardly to meet the medial wall portions 94, 96. From this junction of the lateral wall portions 90, 92 and the medial wall portions 94, 96, the medial wall portions increase slightly in depth in reaching an apex 98 at the front centerline 100 of the upper tray 18.

The depending medial portions 94, 96 of the depending encircling wall 88 of the upper tray 18 are formed on an increased arc 102 in comparison with the formed arc 104 of the upstanding medial portions 78, 80 of the upstanding encircling wall 72 of the lower tray 16, to approximate the anatomy of the human mouth. The higher upstanding back 26 of the lower tray 16 is greater in the up and down vertical dimension than the higher or deeper depending back 32 of the upper tray 18.

The Adjustable Tripod Used With the Dental Articulator

The fourth part of the dental articulator 14 is the adjustable tripod 108, shown by itself in FIG. 5, and shown during its interim use in FIG. 6, in respect to the placement of a lower dental cast 10 in the lower tray 16, which is deeper to accommodate more dental plaster. A T shaped planar body 110 of this tripod has the lateral extending T portion 112 and the longitudinal stem portion 114. Non adjustable depending legs 116, 118 are integrally positioned at the ends of the T portion 112. An adjustable height depending leg 120 is positioned at the free end 122 of the longitudinal stem portion 114. When this tripod 108 is made of injection molded plastic, a metal threaded insert 124 is installed at this free end 122 to provide female threads used in receiving the plastic threads 126, formed in this adjustable height depending leg 120. This leg 120 also has a knurled finger receiving portion 128, in turn serving also as the depending contacting portion 130, joining depending contacting portions 132, 134 of the non adjustable legs 116, 118, which contacting portions together determine the overall angular positioning of this adjustable tripod 108. Indicia on the threads 126 of the leg 120, indicate when five degrees of the cant angle 142 have been changed.

The Method of Use of the Dental Articulator

Using these four parts, 16, 18, 20, and 108 of this dental articulator, dental plaster 136 and resting position registrations 138, a patient's lower dental cast 10 and upper dental cast 12 are positioned in the neuromuscular resting position, which matches the neuromuscular resting position of a patient's jaws, as shown in FIG. 3. Or by not using the resting position registration 138, but using a bite registration 144, patients' dental casts 10 and 12 are positioned in their full teeth contacting centric occlusion position, as shown in FIG. 1.

As illustrated in FIG. 6, a patient's lower dental cast 10 has been placed in dental plaster 136, which previously has been placed in the lower tray 16, sometimes referred to as the lower receptacle 16. Before the dental plaster 136 is too firm, the lower dental cast 10 is moved into the cant of the occlusal plane of a patient's teeth, as determined and recorded from the observance of a patient's lateral cephalometric head X-ray film. During the movement of this lower dental cast 10, the preadjusted tripod 108, set at the patient's cant, designated by number 142, is used in positioning this lower dental cast 10, as shown in FIG. 6. The tripod 108, when finally positioning the lower dental cast 10, is contacting the incisor cast teeth anteriorly and the most terminal cast molars posteriorly, as all of its legs contact the flat working surface 140 of a laboratory bench, thereby duplicating the patient's cant of the occlusal plane.

Also before the dental plaster 136 is too firm, the lower dental cast 10 is aligned in reference to the centerline 84 of the lower tray 16. Thereafter, the dental plaster 136 hardens to complete the positioning of a patient's lower dental cast 10 in the lower tray 16.

Thereafter, in reference to the exploded view in FIG. 7, indicating method steps, in creating a full teeth contacting position of the dental casts 10, 12, the upper dental cast 12 is placed on its respective side of a patient's previously obtained full bite registration 144, taken with the patient's teeth clenched firmly together. Then this combination of the upper dental cast 12 and this full bite registration 144 is placed on the respective lower cast teeth guided by the indentations of the full bite registration, thus completing the establishment of the relation between upper and lower teeth and jaws. Then the soft dental plaster 136 is placed on the top of the upper dental cast 12. Thereafter, the upper tray 18, guided by the legs or columns 62, 64 of the U shaped rigid upright support 20, is gently lowered into the soft dental plaster 136, until the level of the top 86 or base 86 of the upper tray 18 and the top of the U shaped upright support legs or columns 62, 64 are flush.

Or thereafter alternatively, again in reference to FIG. 7, in creating the neuromuscular resting position of the patient's jaws, the laboratory procedure is almost identical to the full teeth contacting position. However, instead of using a full bite registration 144, a tooth guided jaw or rest position registration 138 is used. This jaw registration 138 is obtained, preferably through the use of electronic muscle relaxing and jaw tracking instrumentation, with the patient's muscles at rest, during the formation of this jaw registration 138.

When these neuromuscular resting positions are reached, the separated positions of the lower and upper trays 16, 18 are observed and recorded, using the spacing indicia 22 presented on the flexible legs 62, 64, of the U shaped upright support 20. Thereafter, the jaw or resting position registration 138 is not needed to determine this overall neuromuscular resting position of the patient's dental casts 10, 12, which matches the overall neuromuscular resting positions of the patient's jaws and teeth.

As illustrated in FIG. 1, at the front of a completed mounting of a patient's dental casts 10, 12, using this dental articulator 14, the centerline 84 of the lower tray 16, and the centerline 100 of the upper tray 18, located at the respective midpoint junctures of the respective medial wall, serve as reference lines for reproducing on this dental articulator 14, the same teeth nearby midline relationships, as observed in viewing the patient's mouth.

By mounting a patient's lower dental cast 10, and upper dental cast 12 in the respective selected positions, using this dental articulator 14, the vertical, horizontal, and transverse relationships of a patient's jaws and teeth are readily demonstrable, thereby dramatically emphasizing these very important diagnostic considerations.

I claim:

1. The combination of a dental articulator used to position patients' lower and upper dental casts in either their centric occlusion positions or their neuromuscular resting positions, to measure the distance between these positions, wherein the patient's lower dental cast is positioned at the cant of the occlusal plane of a patient's teeth, and a tripod, wherein the dental articulator comprises:
(a) a lower tray, to receive a patient's lower dental cast, having rear receiving structures;
(b) an upper tray, to receive a patient's upper dental cast, having rear receiving structures; and
(c) an upright rigid support, having extending structures to be slidably and frictionably positioned at selected locations within the respective receiving structures of the lower and upper trays; and wherein the tripod comprises:
(a) a planar body having end portions; and
(b) three depending spaced legs secured to end portions of the planar body, one of the legs being adjustable in height, and the other two legs being equal in height, whereby, the tripod, via adjustment of the adjustable leg, positions the planar body at an angle which is the cant of the occlusal plane of a patient's teeth, and the legs which are equal in height determine the maximum height of positioning the patient's lower dental cast, and thereafter the tripod is used to position the patient's lower dental cast in the lower tray, at the cant of the occlusal plane of a patient's teeth, during the use of the dental aritculator to measure the distance between the centric occlusion position and the neuromuscular resting position.

2. The combination of the dental articulator and the tripod as claimed in claim 1, wherein the planar body of the tripod is T shaped, having a lateral portion having two of the end portions from which two of the spaced legs, which are equal in height, depend, and a longitudinal portion having an end portion from which the one spaced adjustable height leg depends.

3. A method of adjustable placement of a patient's upper dental cast and lower dental cast in their centric occlusion position comprising:

(a) placing a lower tray on a dental working table;
(b) adding dental plaster to the lower tray;
(c) lowering a patient's lower dental cast down onto the dental plaster;
(d) arranging this lower dental cast at the centered position;
(e) adjusting an adjustable tripod to an angular plane, which is the occlusal plane of the patient's teeth;
(f) moving the adjusted tripod over the lower dental cast before the dental plaster has become firm;
(g) tilting the lower dental cast to match the angularity of the adjusted tripod and thereby reach the cant of the occlusal plane of a patient's teeth;
(h) securing upright supports to the lower tray;
(i) placing a registration on the lower dental cast to subsequently reach a centric occlusion position;
(j) lowering a patient's upper dental cast down on the registration;
(k) adding dental plaster to the top of the patient's upper dental cast;
(l) slidably attaching an upper tray to the upright supports secured to the lower tray; and
(m) moving the upper tray downwardly to contact the dental plaster on the top of the patient's upper dental cast, continuing this moving so contact is made between the upper dental cast, the registration, and the lower dental cast.

4. A method, as claimed in claim 3, wherein the moving the upper tray downwardly so contact is made between the upper dental cast, the registration, and the lower dental cast, is continued until the upright supports are flush with each of the trays.

5. A method, as claimed in claim 3, wherein the cant of the occlusal plane of a patient's teeth is first obtained by reading a patient's lateral cephalometric head X-ray film, and thereafter used in adjusting the adjustable tripod.

6. A method, as claimed in claim 5, wherein the adjusting of the adjustable tripod occurs by adjusting one adjustable leg of three legs of a tripod.

7. A method of adjustable placement of a patient's upper dental cast and lower dental cast in their neuromuscular resting position, comprising:
(a) placing a lower tray on a dental working table;
(b) adding dental plaster to the lower tray;
(c) lowering a patient's lower dental cast down onto the dental plaster;
(d) arranging this lower dental cast at the centered position;
(e) adjusting an adjustable tripod to an angular plane, which is the occlusal plane of the patient's teeth;
(f) moving the adjusted tripod over the lower dental cast before the dental plaster has become firm;
(g) tilting the lower dental cast to match the angularity of the adjusted tripod and thereby reach the cant of the occlusal plane of a patient's teeth;
(h) securing upright supports to the lower tray;
(i) placing a registration on the lower dental cast to subsequently reach a neuromuscular resting position;
(j) lowering a patient's upper dental cast down on the registration;
(k) adding dental plaster to the top of the patient's upper dental cast;
(l) slidably attaching an upper tray to the upright supports secured to the lower tray; and
(m) moving the upper tray downwardly to contact the dental plaster on the top of the patient's upper dental cast, continuing this moving so contact is made between the upper dental cast, the registration, and the lower dental cast.

8. A method, as claimed in claim 7, wherein the moving the upper tray downwardly so contact is made between the upper dental cast, the registration, and the lower dental cast, is continued until the upright supports are flush with each of the trays.

9. A method, as claimed in claim 7, wherein the cant of the occlusal plane of a patient's teeth is first obtained by reading a patient's lateral cephalometric head X-ray film, and thereafter used in adjusting the adjustable tripod.

10. A method, as claimed in claim 9, wherein the adjusting of the adjustable tripod occurs by adjusting one adjustable leg of three legs of a tripod.

* * * * *